(12) United States Patent
Goldstein et al.

(10) Patent No.: US 6,998,991 B1
(45) Date of Patent: Feb. 14, 2006

(54) DUAL CARBON MONOXIDE SENSOR SYSTEM WITH CONTROL CATALYST: NEW CO AND HUMIDITY METHOD AND APPARATUS

(75) Inventors: Mark K. Goldstein, San Diego, CA (US); Robert Banach, San Diego, CA (US)

(73) Assignee: Quantum Group Inc., San Diego, CA (US)

( * ) Notice: Subject to any disclaimer, the term of this patent is extended or adjusted under 35 U.S.C. 154(b) by 249 days.

(21) Appl. No.: 10/262,047

(22) Filed: Oct. 1, 2002

Related U.S. Application Data

(60) Provisional application No. 60/326,255, filed on Oct. 1, 2001.

(51) Int. Cl.
*G08B 17/10* (2006.01)

(52) U.S. Cl. .................. 340/628; 340/629; 340/633

(58) Field of Classification Search ............... 340/628, 340/629, 630, 632, 693.6; 422/54; 73/31.01, 73/31.05; 436/134
See application file for complete search history.

(56) References Cited

U.S. PATENT DOCUMENTS

| | | | |
|---|---|---|---|
| 4,043,934 A | 8/1977 | Shuler et al. | |
| 5,063,164 A | 11/1991 | Goldstein | |
| 5,280,273 A | 1/1994 | Goldstein | |
| 5,302,350 A | 4/1994 | Goswami et al. | |
| 5,346,671 A | 9/1994 | Goswami et al. | |
| 5,405,583 A | 4/1995 | Goswami et al. | |
| 5,573,953 A | 11/1996 | Marnie et al. | |
| 5,596,314 A | 1/1997 | Goldstein | |
| 5,618,493 A | 4/1997 | Goldstein et al. | |
| 5,624,848 A | 4/1997 | Marnie et al. | |
| 5,793,295 A | 8/1998 | Goldstein | |
| 6,172,759 B1 | 1/2001 | Goldstein | |
| 6,245,214 B1 * | 6/2001 | Rehg et al. | ................. 205/764 |
| 6,251,344 B1 | 6/2001 | Goldstein | |
| 6,429,019 B1 * | 8/2002 | Goldstein et al. | ........... 436/134 |

* cited by examiner

*Primary Examiner*—Toan N. Pham
(74) *Attorney, Agent, or Firm*—Christie, Parker & Hale, LLP (57) ABSTRACT

The present invention is a new sensor system with catalyst for control and one with a dummy catalyst. An apparatus and method for rapidly determining the concentration of CO, water vapor, and temperature. One of the major reasons to rapidly determine a small but sudden rise CO is for fire detection. The combination of the CO, followed by rapid relative humidity rise is a clear indication of possible fire or an appliance malfunction, blocked flu or other combustion process gone awry. If the incident is accompanied by ions or particles that would be smoke from a fire. The signal from the CO determined by numerically compensating for humidity changes. Any one or two parameters could cause an increase the sensitivity of the other in a fire detector such as combination CO, relative humidity, temperature and smoke detector. Another application for rapid CO detection is in a vehicle to protect the occupants from a catastrophic CO event. The preferred embodiment by means of optically monitoring the control and CO responding sensors that respond to the CO by means monitoring the optical change to the humidity in one and humidity and CO in the other and provide a means to remove the humidity.

8 Claims, 5 Drawing Sheets

DUAL CARBON MONOXIDE SENSOR SYSTEM WITH CONTROL CATALYST: NEW CO AND HUMIDITY METHOD AND APPARATUS

CROSS-REFERENCE TO RELATED APPLICATION

This application claims the benefit of U.S. Provisional application No. 60/326/255, filed on Oct. 1, 2001.

The novel method uses two sensors such as the K series sensor, each in a separate chamber such as a MicroSIR each having at least one LED and a photodiode. The two chambers, one with a getter, catalyst and sensor; the second with a getter pseudo catalyst and sensor are illuminated by independent LEDs and viewed by independent photodiodes. The pseudo catalyst is made of the same composition as the catalyst except it lacks palladium, which is necessary to convert CO to carbon dioxide in air. By using the same materials as substrates and other coatings with only one small exception the diffusion paths are kept the same. These two K sensors are matched pairs in response and photon transmission, so that the effect of CO can be subtracted from the effect of CO plus humidity.

The use of visible and IR LEDs has some advantage but is not necessary in all cases. In the inlet to the first chamber that measures RH only, there is a K catalyst that converts all background CO to CO2. This control sensor is used to measure RH directly so it can be used to calculate the CO concentration from the other sensor by means of a simple microprocessor. One such method is to simply subtract the RH sensor signal from the second sensor, which responds to both CO+RH. The second sensor measures both RH and CO. Thus the rate of response of the RH component in both are very close except for an effect caused by the interaction of water with CO in the catalyst.

There are a number of applications where fast and accurate resolution of CO and humidity are important such as residential CO detectors, fire detectors, fuel cells, breath diagnostics and digital CO monitors. Fast CO sensing devices are also important for vehicles, combination CO/smoke detectors as well as many other applications, which can respond to CO or other gas exposures in a number of ways to protect people and other living things. In addition, these 2K sensors can be used to control ventilation. Some air purification systems need a fast sensor to actuate an on off switch and control motor speed. These air cleaners can reduce the level of ozone, particulate matter, hydrocarbons, CO, CO2 and other pollutants.

Reference: Detection Apparatus and Method (CO/SMOKE product) U.S. Pat. No. 5,793,295 Aug. 11, 1998; U.S. Pat. Nos. 5,063,164, 5,302,350, 5,596,314 and U.S. patent application Ser. No. 09/260,181 (fast sensor regeneration for BSI standard) filed Mar. 2, 1999, Ser. No. 60/110,898 filed Dec. 4, 1998 (getter system for ammonia), Ser. No. 09/105,544 filed Jun. 26, 1998 (air quality and RH).

FIELD OF THE INVENTION

The present invention relates to a sensing system capable of measuring RH and CO concentrations, which comprises two optical responding sensors. The system consists of at least two separate sensing chambers for the rapid detection of CO and relative humidity.

This field relates to a sensor and a sensing apparatus incorporating at least two sensing chambers. One with a CO oxidation catalyst such as 10K and the other a dummy catalyst, which comprises all components exactly, except no palladium. Other noble metals that do not oxidize CO at these temperatures in this chemical matrix may be substituted for palladium in the dummy catalyst. The optical response from the IR LED in the K sensor with the catalyst is a measure of RH, while the other optical response includes both CO and RH. The use of single humidity control device with two separate chambers and air entry is also feasible as described below.

We can separate the humidity effect from the CO effect by storing values in register of a microprocessor. The operation of a circuit and software algorithm will allow the calculation of both CO and relative Humidity (RH). For example, by taking derivative of the optical response with respect to time, $dI/dt$, i.e., by measuring the values of the photon intensity I (n1) at time t(1) and I (n2) at time t(2). The subtracting the RH component can be done either from the photon intensity or a look up table may be constructed.

To construct the look up table certain experiments need to be conducted under controlled conditions. First the two sensors are constructed one with a catalyst and the other with dummy catalyst. They are monitored in the lab under a number of different percent relative humidity (% RH) and each humidity is tested at a number of CO concentrations. These tests should be conducted at the test point of any standard that the product is being developed for such as UL 2034. These tests will also be conducted at a number of different temperatures.

If we measure the CO concentration in a test chamber, we have a known valve of CO for every value of voltage or percent transmission; however, these values do change over time so we can attempt to measure the slope and it is related to the CO concentration [CO]. Next we need to control the relative humidity (RH) in the chamber and measure it as [RH]. Now we have output from sensor 1 with catalyst and sensor 2 with dummy catalyst. Sensor 1 with the catalyst is the control because the CO is consumed before it can react the sensor; however this sensor output value is related to humidity and any changes in RH. Next we set up the following equations for each of the following RH values in a table and solve for f the fudge factor.

| | Sensor outputs | | |
|---|---|---|---|
| Actual RH % | CO sensor 1 | RH(f)Control Sensor 2 | CO level ppm |
| 5 | CO | - H x f(5) = | [CO] |
| 10 | CO | - H x f(10) = | [CO] |
| 20 | CO | - H x f(20) = | [CO] |
| 30 | CO | - H x f(30) = | [CO] |
| 40 | CO | - H x f(40) = | [CO] |
| 50 | CO | - H x f(50) = | [CO] |
| 60 | | . | |
| 70 | | . | |
| 80 | | . | |
| 90 | | . | |
| 95 | CO | - H x f(95) = | [CO] |

Since we know the carbon monoxide concentration [CO] and the percent relative humidity [% RH] in the chamber we can calculate the factor f at each relative humidity in the table. This table can then be made into a look up table in a simple low cost microprocessor. This low cost computing apparatus and method allows a variety of outputs including digital.

Various parameters of interest may be calculated as described in more detail below such as gas concentration, Traveling Weighted Average (TWA), peak concentration over some predetermined time interval, total dose from target gas exposure, etc. The information may be stored in the microprocessor for down loading at a later time or displayed on a digital readout system also described below.

The field of the invention relates to CO gas monitoring devices for a wide variety of applications, such as home safety, occupational health, industrial, commercial, energy, recreational and medical.

The present invention relates to a sensor system to accurately detect CO over wide ranges such as 10 to 15,000-ppm. The big advantage of the K sensor over the biomimetic sensor is speed of response and range. Although this technique and novel apparatus described below is not limited to K series sensors.

This basic concept can be used to detect humidity or CO and RH depending on the configuration and application. The use of getters to precondition these samples may selectively remove some gases as a way to enhance selectivity and accuracy.

These CO and other detection devices may be incorporated in or attached to various vehicles and may be portable units such that it can be easily carried for applications in locations other than the vehicles or from one vehicle to the other. This invention includes applications comprising gas detector systems such as a carbon monoxide (CO) sensor to detect the presence of dangerous levels of CO. By Applying other gas detection systems other than those described for CO to the substrate the detection system can be used for other gasses in variable humidity environments.

In addition, a signaling means may be incorporated to alert the people. The novel cat system with K series sensor device can be used to display digital information, e.g. concentration of CO and % RH, compute and/or display the Time Weighted Average (TWA), peak concentration over some predetermined time interval, total dose from CO exposure, and relative humidity. In addition, the information may be displayed on the vehicle dash or other location either in digital or analog.

The field of the invention involves gas monitoring with two sensing chambers containing nearly identical sensors.

The K series sensors typically have copper concentrations more 1000 times greater than previous sensors described in U.S. Pat. No. 5,063,164, herein incorporated by reference. The use of the high copper K sensor is also described in U.S. patent application Ser. No. 60/219,271 filed Jul. 19, 2000 and application Ser. No. 09/800,107 filed Mar. 5, 2001, herein incorporated by reference.

These K series sensor with high copper concentrations respond in the infrared and visible differently. This difference may also be used to calculate the CO concentration and percent RH accurately. Another way to measure CO accurately and reliably from below 10 ppm to 10,000 ppm is to employ a catalyst in the reference sensor. The reference sensor was invented that responds to the environment in manner almost identical to the K sensors except no CO response occurs in response to CO because there is a CO catalyst in front of that sensor, which converts the CO to carbon dioxide.

In the reference sensor the catalyst system preferably includes a means to convert the CO to carbon dioxide that does not effect humidity in the sensing chamber. Within the enclosed space of the reference sensor the humidity is the same as the CO sensor chamber because a dummy catalyst is used to control the diffusion rate and effects on RH. A catalyst composition resembles to 10K CO catalyst, which is also a subject of a co-pending application entitled "Carbon Monoxide Catalyst System to Remove CO for Fuel Cell and Other Applications" field Jul. 10, 2001 herein incorporated by reference.

Both sensors' chemistries are applied to a high surface area substrate that is transparent; however, the catalyst is made of small particles and thus will convert CO to carbon dioxide efficiently before it enters the reference chamber regardless of which sensor is used. For example, the CO catalyst chemistry may be applied to a standard SPS substrate and later ground or it may be pre-ground before the application. Other substrates such as silica gel, aerogel, activated carbon, alumina or cellulose material may be used. The catalyst is held in an air filter frame just above the sensors and below the air inlet system.

Because the CO is a dependent variable, which also depends on the RH values, it may be necessary to iterate the calculation to provide the best accuracy of the CO and RH value. In approximate method a look up table can be used as discussed above. To determine the table laboratory measurement can be store in a microprocessor's look-up table.

These sensors are responding to both RH and CO in the near IR e.g., 940 nm.

The range of these sensors is defined by the threshold level, i.e.; the sensors operate below threshold. The 2k sensor has a threshold about 2,000 ppm CO and the 10K sensor at about 10,000 ppm. The reference sensor response to humidity is nearly identical to the humidity response of CO sensor with dummy catalyst. The threshold of the high copper CO sensors may be 200 ppm or 20,000 ppm.

BACKGROUND OF THE INVENTION

The most ubiquitous pollutant found in air is CO; the CO danger is well known in home, workplaces and vehicles. Over 1100 people lose there lives do to carbon monoxide (CO) generated by vehicles annually according to the Cobb and Etzel JAMA Aug. 7, 1991 Vol. 266, No. 5. According to the EPA's "Air Quality Criteria for Carbon Monoxide" Published in 2001 on the Internet, stated that 3.75 million workers are exposed to dangerous levels of CO in the workplace from engine exhaust in just one year. The Center for Disease Control experts Cobb and Etzel found that over 5,600 people are recorded to die from CO according to the death certificates database. Michael Dolan states that these fatalities are grossly underestimated. He found that 23.6% of those people diagnosed with the flue by doctors actually had CO poisoning. This work by Dolan and others (Heckerling) demonstrated that CO poisoning is poorly diagnosed by doctors. Therefore there is a need for more accurate and reliable CO sensors.

In 1993, according to the National Highway Safety Traffic Administration (NHSTA) over 100 people lost their lives as a result of CO while the vehicle is moving. Princess Diane's driver was poisoned with CO as proven by a test on his blood indicating, i.e., about 20% carboxyhemoglobin (COHb). The CO poisoning was discovered because of the exceptional attention given to this case.

Goldstein and another described one example of a CO sensing means by Goldstein et al. Both disclosed biomimetic sensors in U.S. Pat. No. 5,063,164 and U.S. Pat. No. 5,618,493, the contents of which are incorporated by reference. These biomimetic sensors mimic the human response to CO. This chemistry was an improvement of an earlier invention by Shuler and Schrauzer, i.e., U.S. Pat. No. 4,043,934. The Shuler and Schrauzer Patent also teaches the use of a chemistry with high copper ion concentration to convert CO to carbon dioxide even at room temperature.

Shuler Schrauzer catalyst has limited life and operates over a narrow range of relative humidity and is not very effective compared to the 10K catalyst as shown by the comparative data.

U.S. Pat. No. 5,063,164 teaches that in the presence of the CO gas the level of danger from the hazardous exposures may be determined by monitoring the sensor with a photon source. By passing photons of a specific spectral region through the sensor and monitor the intensity of the photon beam or use a pulsed photon source to conserve power such as an infrared LED combined with a simple photon detector such as a photodiode. There are a number of other gas sensors that have been disclosed in the following U.S. Pat. Nos., e.g., 4,043,934, 5,346,671, 5,405,583, 5,618,493 and 5,302,350, which can detect a target gas such as CO by monitor the optical properties of the sensor.

Goldstein described several CO detector systems, which incorporate these types of optical changing sensors. For example, the biomimetic sensor was discussed in U.S. Pat. Nos. 5,280,273, 5,793,295 and others such as by Marnie et al disclose a low cost circuit (Apparatus) with software and method for detecting CO in U.S. Pat. Nos. 5,573,953 and 5,624,848. Goldstein et al further disclosed a digital and rapid regenerating means in co-pending patent applications Ser. Nos. 60/051,038, 80/026,34 and 60/076,822 herein incorporated by reference. The gas detector system includes a housing containing photon sources, which emits photons in at least a region of the electromagnetic spectrum that the sensor absorbs in response to the CO exposure. A photodetector sensitive in the corresponding active region of the spectra a circuit designed to measure the response and a noisemaker or other signaling means is used. The signaling means is actuated by circuit and software system. The housing (enclosure) has at least one opening to permit the sound to escape and the entry of CO or other gases. The detector also contains a sensor, which may be a permanent type sensor or may be configured with a battery for convenient replacement or may be mounted within the housing designed for easy replacement. Several systems are disclosed in U.S. Pat. No. 5,793,295 by Goldstein issued in Aug. 11, 1998 and is hereby incorporated by reference. Goldstein also described in Aug. 11, 1998 patent U.S. Pat. No. 5,793,295 a CO/smoke detector that increases sensitivity of smoke in the presence of CO. The new novel Co/smoke has a light trapping system, which comprises curved fins of black plastic so that smoke has easy access from all directions. This is an improvement over the Co/Smoke alarm described in U.S. Pat. No. 5,793,295 in which a dropping resistor is used to enhance the air flow through the smoke chamber with a heating chimney effect. Therefore the new device is useful for battery power; AC power; 12-volt low power system as well as AC with battery back up. These combinations and multiple sensing fire detection systems may function better with two K series sensors each in a separate chamber. Although the edge-looking view with the S34 with 20 percent spike of silicomolybdic acid and paladium was shown to be quite fast at 550 ppm with alarm time of 20 seconds or less, they cannot detect 20 ppm in 2 minutes, which is important for fire detection.

The cross fertilization fire detectors has not been commercialized yet although it was designed, the S sensor cannot be made both sensitive enough to detect a 20 ppm CO rise above ambient without false alarms and have a reasonable life. The slower speed of the S sensor makes it difficult for a system to fix the exact location of the CO rise and then compare it with ambient conditions. The near instant response of the K sensor is ideal for larger system in which it is possible to compare the rise of one or two sensors with appropriate software as discussed above and below. The K sensor is expected to last longer than the circuit, which is estimated at 10 years maximum with high confidence. Therefore, this novel CO-smoke is much more practical and useful than other CO smoke detectors. Currently First Alert is marketing a combination CO detector, which contains the Quantum S34 sensor and software. The new K sensor allows the manufacture of a lower cost, better performing CO smoke detector.

Several low-cost biomimetic sensors are disclosed in U.S. Pat. Nos. 5,063,164, 5,624,848 (Marnie et al), systems U.S. Pat. No. 5,618,493, (Goldstein et al), U.S. Pat. No. 5,280,273 (Goldstein), U.S. Pat. No. 5,793,295 (Marnie et at). These software systems will not work with the K series sensors. Higher performance advanced systems are disclosed in co-pending applications Ser. No. 60/076,822 filed Mar. 4, 1998 and a digital CO detector PCT/US97/16846 Filed 19 Sep. 1997 the contents of which are hereby incorporated by reference. The new K sensor with catalyst and dummy catalyst system can meet the needs of the market place.

The above K series CO sensor catalyst technologies may be incorporated into the small size CO detector or digital monitor. The K series cat-sensor is excellent for use in ventilation controls, medical devices, fuel cells and digital monitors as well as fire alarms.

In addition, the customer may incorporate the K-series sensor and operating circuitry into an automobile before it is purchased. This CO and other gas safety device may be incorporated in the passenger cabin or elsewhere in the vehicle. In some cases, a dual sensor system may be used so that a "smart" vehicle can protect its passenger from the effects of CO containing smog in the outside environment as well a vehicle generated CO. There may be one sensor inside and a second sensor outside the cabin. When the outside is indicates higher levels than inside the vents can be shut (and the windows closed) the air re-circulated, optionally through a catalytic means to convert the CO to carbon dioxide. The catalyst is described below.

Several Low cost embodiments of this invention incorporate one cat-K and one dummy-K sensor, a low power consuming sensor monitoring system used for detecting the presence of a predetermined carbon monoxide ("CO") concentration and humidity.

These sensors comprise at least one self-regenerating sensing reagent coated onto a substrate, for example, a high surface area transparent material such as a porous glass, sol-gel silica or SPS (silica porous substrate manufactured by Quantum Group by a trade secret process. The SPS substrate consist of a porous solid silica material, which is sufficiently transmissive to a specific range of photons in the specific wavelength region to interest, i.e., visible and near IR. The SPS substrate is coated with the K sensor material by a self-assembly process. The K sensor is used to detect the optical characteristic changes in the sensor using an optical source such as a light emitting diode and a photodiode. These optical components and sensor(s) are controlled by a circuit designed to measure the output of the photodiode monitoring the sensor which would alert the passengers through some means and actuate controls as programmed depending on the level of hazard or condition.

Another embodiment is a modification of embodiment 1, e.g., based on dI/dt Plus IK, where I is equal to the intensity of photons and K is a constant. Under certain conditions the derivative of the transmitted photon with respect to a time interval plus the actual transmitted photon intensity is proportional to the carbon monoxide (CO) concentration, $[CO] = k_1\{dI/dt\} + I(K_2)$ at other times $[CO] = k_2\{I(n)\}$ When $dI/dt$ is very near zero and when $dI/dt$ is not linear such that the second derivative is not very near zero then the sum of the two, i.e., $I(n)$ and $dI/dt$ is divided by 2 or by an average or mean, in addition a weighted average is feasible such as represented by the general equation:

$[CO] = c\{k_1[dI/dt] + k_2[I(n)]\}$

The approximation can be employed easily and can limit the cost of the alarm or detector and has the capability of digital display.

Other approximations are also possible, e.g., the sum of averages or weighted averages over a series of registers $[CO] = k_1(dI/dt) + K_2[I(n)]$ There are two basic optical techniques that can be incorporated as embodiments of the optical monitoring method, i.e., 1) transmission as discussed above and 2) reflection a second embodiment of this invention.

Let us describe the photon transmission method, as it is generally preferred. This method can be used for a variety of gases for which a similar responding optical sensor exists; however, as an example carbon monoxide (CO) will be discussed as the target. by this exemplary focus on CO we in no way intend to limit the target gases of this method. This method maybe useful in producing digitally displayed CO concentrations.

A third embodiment of the invention is a fixed point detector (which has been calibrated to go into alarm or warning when the sensor optical properties change past some point that is preset during calibration) and measure the sign of the derivative $dI/dt$ to know when to stop alarming.

In the absence of CO concentration above the threshold concentration, which is defined as 2000 ppm for the 2K sensor, the K series sensor will operate properly unit it reaches or exceeds the threshold. The system can use more than one sensor, e.g., if the 2K is exceeded the monitor can be automatically switch over to a 5K sensor and so as needed. Only one reference sensor should be needed.

Most of the current portable digital gas detection products with acceptable accuracy (plus or minus 2%) on the market are battery operated and use electrochemical cells for sensors. Units that are accurate are expensive, typically $500 to $1000, require frequent calibration, and frequent sensor and battery replacements. These electrochemical units can not operate at −40° C. nor can they live for long periods of time at 70° C. Metal oxide Semiconductor sensors take very large amounts of power and therefore cannot be operated for a reasonable time of 2 years on a small 9 volt battery. The MOS sensors are subject to interfering gases and also lose sensitivity when exposed to silicones often used in the automotive industry. Therefore there is a need for a low cost, reliable, low power, accurate, easy to use battery powered unit to detect various gases such as CO especially a unit that can be incorporated in an automobile or other vehicles. There is a need to incorporate the product into new fire detectors because 70% of all fire deaths are CO related.

The K series sensor operates from temperature ranges from minus 40° C. to +90° C. and from nearly zero to 100% relative humidity, when the reservoir system is employed.

Acid gases such as sulfur dioxide, sulfur trioxide, oxides of nitrogen, and similar acid compounds may be removed from the air stream by means of a getter comprising a porous air filter mater impregnated with acid reacting chemical such as sodium bicarbonate, sodium carbonate, calcium carbonate and magnesium hydroxide. In addition, a filter section or getter may be designed to react with bases such ammonia. Getter may consist of citric acid, tartaric acid, phosphoric acid, molybdosilicic and other acids such as phosphoric, polymeric acids impregnated on silica gel or other suitable substrate such as felt. The preferred embodiment of the ammonia getter is the subject of a co-pending application Ser. No. 60/110,898 filed Dec. 4, 1998 by J. Ryu and Paula Johnson. A layer of charcoal may separate the acid from the basic layer, A useful air purification system may include 4 to 5 active layers separated by inert material such as a porous felt. The air purification system is also the subject of a co-pending application Ser. No. 09/105,544 filed Jun. 26, 1998.

One skilled in the art may appreciate a low powered CO sensing control apparatus which can also measure and display digitally the gas concentration by calculations from the response of optically responding RH and CO+RH sensors. Currently, there are no selective digital CO detection products that can operate for many years with common batteries such as 9-volt alkaline. Such an apparatus and method would increase the desirability of a wide variety of products from home safety detectors to personal monitors, medical products, breath diagnostics to industrial controls to automotive gas sensing products, to safety shut off systems for appliances and controls for ventilation systems.

BRIEF DESCRIPTION OF THE DRAWINGS

The invention will be better understood with reference to the following detailed description and accompanying drawings wherein.

SUMMARY OF THE INVENTION

Several preferred embodiments of the present invention are described herein. The invention is an apparatus and method for determining the concentration of CO rapidly and accurately.

The preferred embodiments uses very little electric power. The sensor has a long life of over 10 years and will operate at −40° C. to +90° C. The use of a K series sensor system may be adapted to minimize humidity and contamination effects. The sensor responds to CO by a change in its optical properties.

The sensor(s) contain molecules in the form of self-assembled supramolecular complexes, which are in the form of a thin layer coated onto the surface of a porous transparent element. Optical properties change in response to CO. These sensing elements rapidly return to the normal color once clear from CO above the threshold. The sensor does not turn blue unless the CO is above the threshold.

There are many ways to monitor these sensors as described below. The use of filters to remove common acid and basic gases as well as volatile organic compounds. Examples of filters include activated charcoal and other getters described in previous patent applications.

For example, a low power application of the invention includes the steps of intermittently measuring the optical characteristics of both the control and CO responding sensor, differentiating a plurality of measurements over time to obtain both the control $Ic(n)$ value(s) and CO responding sensor $Is(n)$ at time $t(n)$. The effects of humidity response seen in the control sensor subtracting it from the CO responding sensor should give a value proportional to the CO concentration. The CO concentration information may be calculated by means of a look up table or may be calculated by an algorithm and then displayed by any display means of choice.

Exemplary apparatus according to the present invention for implementing the method including a series of LEDs and photodiodes with 2 CO sensors located so that the photons pass through EACH sensor and the amount of light transmitted is measured by the photodiode response to that light. Each LED illuminates a corresponding sensor the same and the light transmitted through the sensor is received by separate photodiodes the same.

For a low-power, low-cost, embodiment of the invention designed to determine the concentration of CO, it is desirable to change the analog signal to digital (at very low power and low cost). The resulting photocurrent from the photodiode is proportional to the transmitted light received by the photodiode, which charges a capacitor. The time to charge the capacitor is related to the CO level.

To produce digital information from the analog signals an analog to digital converter is required. These may be incorporated into the microprocessor or may be separate. The method of measuring the charging time of one or more capacitors can also be used to produce an analog to digital signal as discussed above.

In addition it is useful to be able to turn on the catalytic converter within a closed environment when CO levels are above about 9 ppm. In order to be alert to this problem early so that the occupant of a vehicle may be provided a maximum of protection, it is useful to sense the CO in the cabin and outside. Thus if a car enters a tunnel, the smart vehicle system can sense the problem, send a signal to the central control, which in turn closes the vents and windows. At the same time the air in the cabin is re-circulated more rapidly through the novel catalyst system that converts the CO to carbon dioxide. The outside CO sensor is again useful to measure inside verses outside, thus telling the vehicle central control when it is safe outside, e.g., when emerging from a tunnel and the air is cleaner outside then inside. The control can then open widows and or vents to clean the vehicle quickly.

Several methodologies will be described in general and then each figure will be described in detail.

A fixed-point detection system is the simplest and can be manufactured at a low cost. When CO is present in sufficient concentrations and for a long enough time, the sensor absorbs photons such that the light transmitted to the photodiode is reduced to a certain value $I(n)$ and then levels out if the amount of CO is constant, and/or its exposure is insufficient to cause the sensor's transmission to drop below the design switch point (e.g. 30% transmission) where the system automatically switches to the next most sensitive sensor in the series to be able to indicate the CO concentration to those trying find the source of CO.

Another gas detection system employs a means to measure the light transmitted through the sensor system at time t as $I(n,t)$ and the rate of change of the CO sensor component $dI/dt$, which may be determined by subtracting the humidity from control sensor from the CO responding sensor. One example is a microprocessor based the detection for rapidly determining CO concentration, $$[CO]=K\ f\{I,dIdt\}$$

over the range of interest for any particular sensor if the second derivative is close to zero $[CO]=k\{dI/dt\}$ for a special case of constant CO but not leveling off before reaching 25% or some similar number indicating the linear range of the sensor.

$[CO]=k\ \{k_2\ dI/dt\ b+k_1\ I(n)b\}$ where b is a constant of that particular sensor and k is equal to one half (½).

One way to calculate CO with a large microprocessor is to fit the empirical data to a type of differential equation, exponential equation, polynomial or similar equation that fits the data, a second approach is to use a look up table.

In one preferred embodiment a microprocessor is used to determine the points and time of the sensor readings, in such alarm or some other action level and to store recent data of $I(n,t)$ and $dI/dt$ for the most sensitive sensors, which are in the linear region, and further to determine which equation or look up table to use within the microprocessor system.

One preferred low cost method of monitoring optical sensor characteristics is to determine the optical change at intervals of time. The rate of change may be expressed mathematically (delta t) or ($\Delta t$). Values may be pre-calculated and placed in some type of look up table.

Alarms made with the fast (K-series) sensor may be designed not to respond to low levels of CO by circuitry design or by microprocessor software or both. Some standards require no response to 30-ppm for 30 days.

The basic method to obtain accurate digital information is to fit an equation to the empirical response data of the sensor (simplify as necessary) and then use the algorithm for the response curve and the regeneration curves, respectively. If the forward reaction rate and reverse reaction rate are different (as they usually are different) separate equations are used. To better illustrate the invention a series of example CO exposures will be examined.

When the CO concentration decreases below the threshold of a responding sensor or clear air is restored, the sensor reverses its optical transmission to its initial optical response at some rate which is indicative of the immediate CO ppm in that environment. The greatest rate of return is examined first followed by a calculation and/or a look-up table operation to determine the CO concentration.

The preferred embodiments of this invention vary widely depending on the application, e.g., for a low cost CO alarm a fixed alarm point is feasible. However, a detector may also be designed to display digitally the levels of CO. Digital display or other warnings may be permitted, even though the level of CO may be well below that which determines an alarm, warning or other action level(s). There are very good reasons to provide such additional features, because a significant portion of the US population is in a high-risk group for CO exposure. These high-risk people include the very young, old, cardiovascular impaired, respiratory impairment, and those that have blood disorders. The sensitive population are seriously affected by even 2 to 4% COHb, Allred, E. N., et al, New England Jr. of Med. 321:1426–1432 1989 and Allred, E. N. et al, Environmental Health Report et al, 91:89–132, 199.

By this general method of operation, the level of sensed CO is determined by measuring the rate of change of light transmission and the value of light transmitted, i.e., through the result of the subtracted CO sensor dI/dt and I(n,t ). The alarm can be designed to silence depending on the sign of the slope of the sensor, which changes in seconds in clean air.

The carbon monoxide (CO) sensing element, manufactured by Quantum Group Inc., has the shape of a disk, which changes the light transmission or absorption when exposed to CO. Also, there are two kinds of sensors: one is the S-series, e.g. the S34 biomimetic sensor and the other is K-series such as 31K.

The S34 sensor is currently employed in most of Quantum's commercial and residential single station CO alarms. The detection mode records the decrease in the infrared light transmission through the sensors, in the presence of CO. The method of detection allows a system to correlate the rate of change in light transmission plus the absolute value of light transmission through the sensor into CO concentrations. The S34 sensor has a relatively slow response to the CO, but is very reliable and suitable for all residential and commercial CO alarms such as those that meet the UL 2034 and 2075 effective Oct. 1, 1998.

The K series sensor response in the near infrared is opposite the S-series sensors, i.e., the transmission increases in the presence of the CO. The K sensor does not become saturated in the measurement range, e.g., from 0 to 2000 PPM for the 2K sensor or 0 to 10,000 PPM for the 10K sensor, no matter how long it has been exposed. The practical time response for 100-ppm CO is less than 10 seconds, and may be less for higher concentrations. The K sensor makes an ideal candidate for a fast response device, such as integrated CO/Smoke that increases the sensitivity of the smoke detection circuit as soon as 15 to 20-ppm CO level is detected. In a system detector part of a series of combo CO smoke detector the reliability is substantially increased because the increase above the ambient is calculated for a given locality versus the average of other detectors in the system.

A disadvantage of the K sensor is that the infrared transmittance or absorption varies with the relative humidity of the test environment. This humidity effect can be turned into an advantage by using two LEDs with each emitting at a different wavelength, one in the infrared and one in the visible, such as red. Other visible LEDs may be used such as orange, yellow and green. For example, when the CO concentration increases the light transmission increases in infrared and decreases in red. When the relative humidity increases the light transmission increases in both red and infrared independent of the CO concentrations.

DETAILED DESCRIPTION OF DRAWINGS

Figure 1:
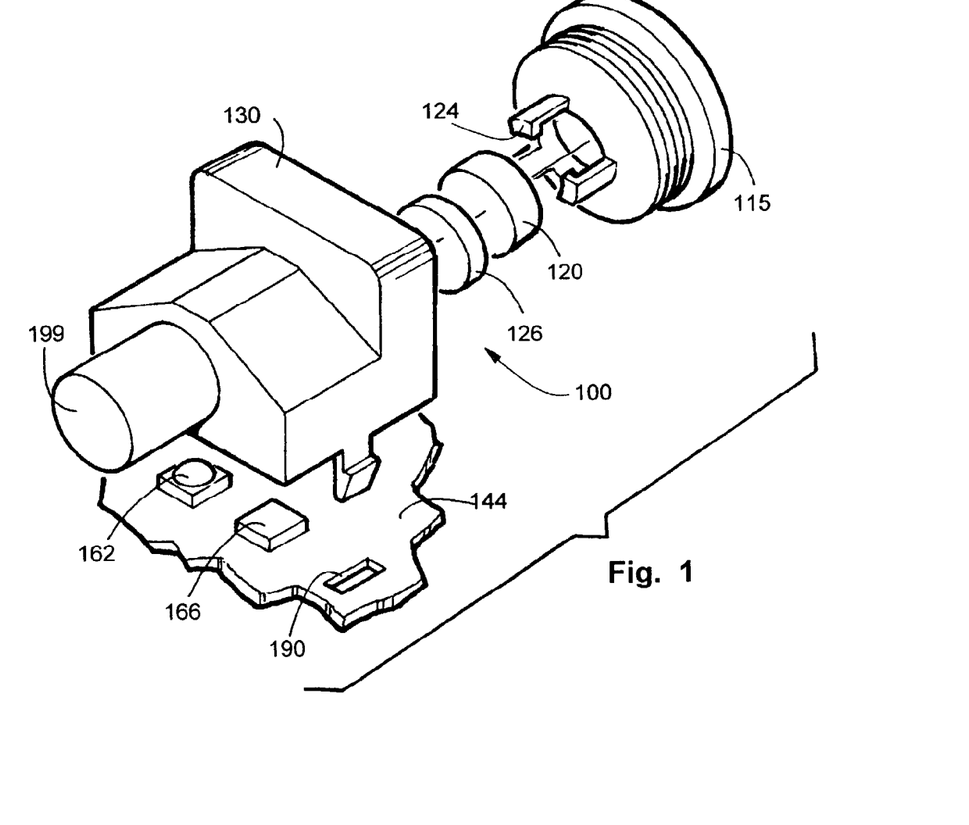
FIG. 1 is a perspective view of an apparatus incorporating the K sensor with the catalyst between it and the atmosphere.

FIG. 1 is a perspective view of an apparatus 100 incorporating the K sensor 120 with the catalyst section 115 between it and the atmosphere and this sensor 120. The housing 130 allows air to diffuse into the sensor through getter not shown, which is located in the catalyst section 115. There are holes in the catalyst holder 115 that regulate the diffusion along with the getter, catalyst and path length. The fingers 124 on the catalyst housing hold the sensor 120 against the shock absorber 126. The alignment of the sensor 120 is in the center of the optical path created by LED 162 and photodiode 166. Optically, there may be a reservoir 199 attached to the back face of sensor housing 130. This part may be threaded or may be a part of 130.

Figure 2:
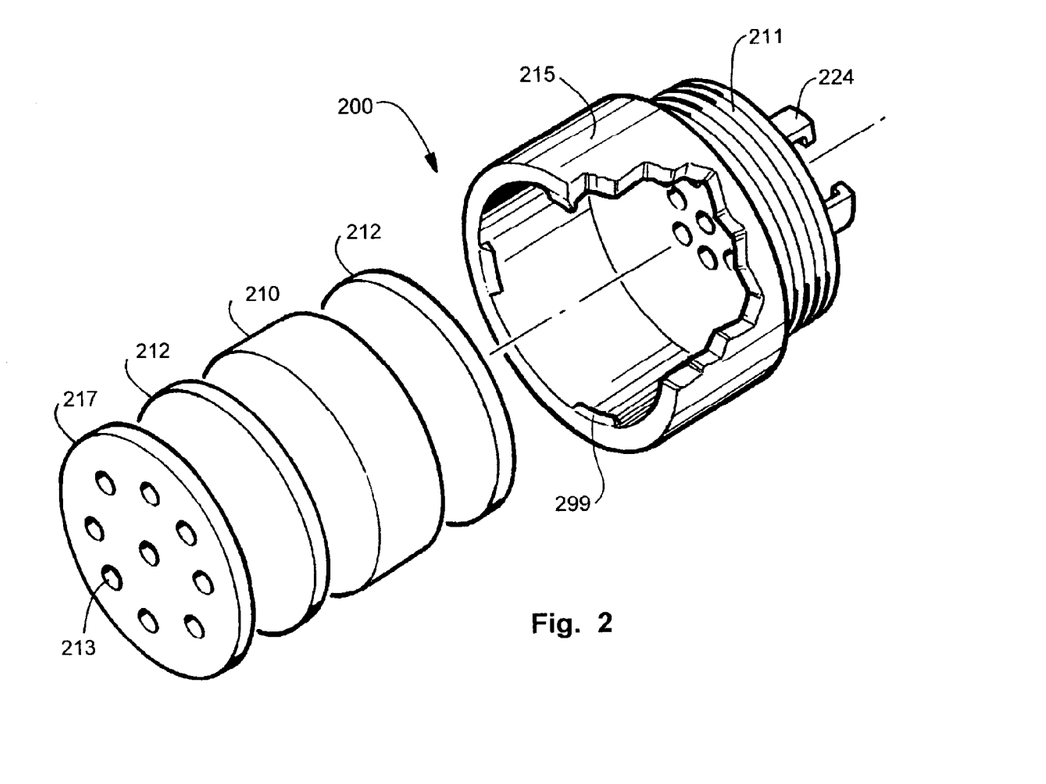
FIG. 2 shows a blow-up of the CO catalyst sections.

FIG. 2 shows an assembly drawing of the catalyst section 200. The catalyst 210 may be a monolith, powder, beads, granules or pellets. This is a getter 212 that filters the ammonia and other basic gases from the air and prevents damage to the catalyst and the sensor not shown here. The getter is on both sides of the catalyst and the system is held in by a porous plate 217 that may take the form of a plate with holes 213. In addition this plate 217 maybe held by tabs on the main housing 215. The housing may be threaded 211 so as to seal when it is attached to the sensor system not shown here. The main catalyst housing has holes 213 at the bottom and also has fingers 224 to hold the sensor not shown here.

Figure 3:
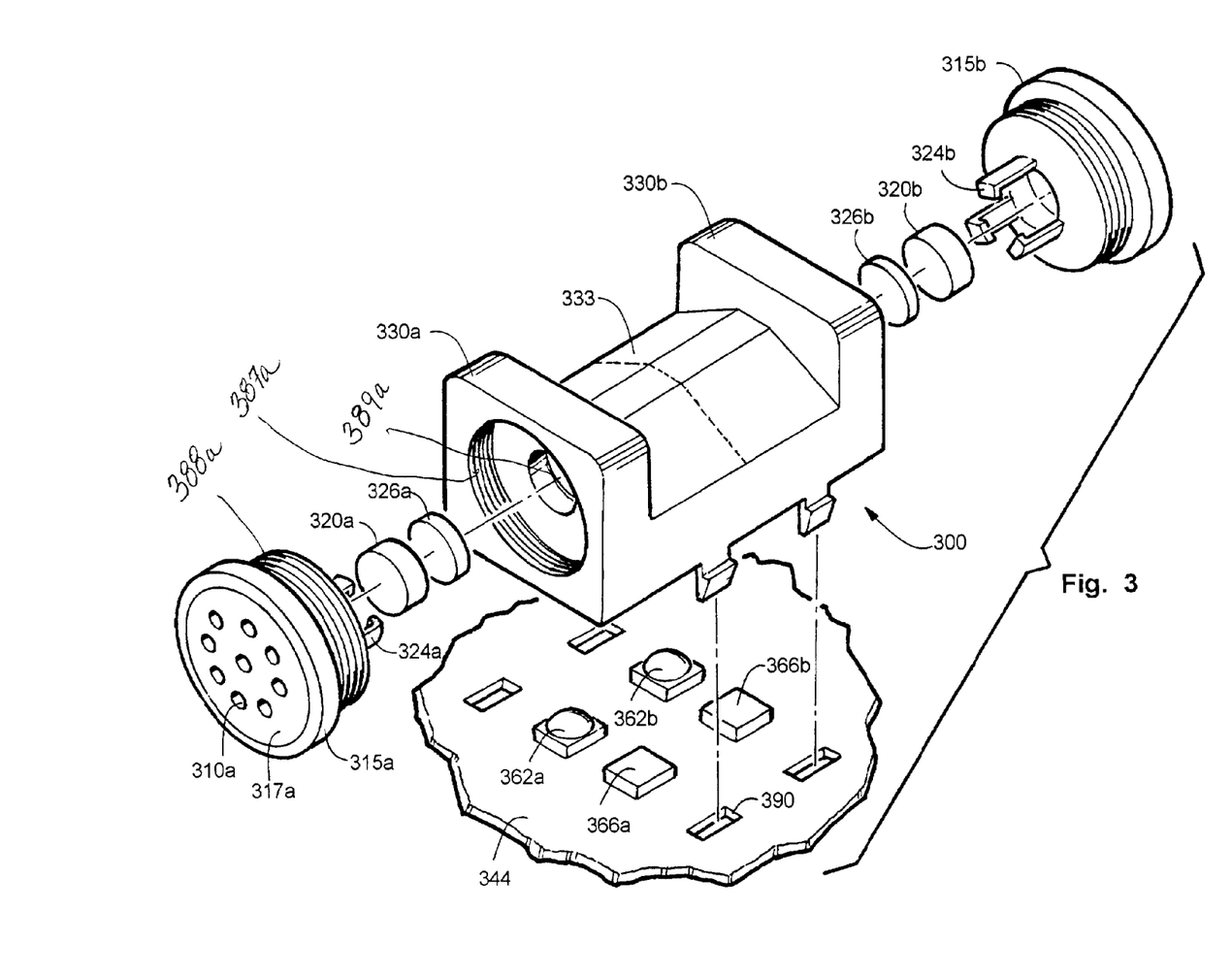
FIG. 3 shows two pairs of infrared LEDs and photodiodes surface mounted to the PC board.

FIG. 3 shows both a CO and humidity sensor 326a with dummy catalyst 315a and the RH sensor 326b with catalyst 315b. This drawing also shows LEDs 326a and 362b and photodiodes 366a and 366b, which monitor both the CO AND RH sensor 320a and the RH sensor 320b. The main housing body comprises clips that can be used to attach the sensor system to the PC board 344 by four slots or holes 390. In addition, the fingers 324a and 324b hold the sensors in place between the shock absorbers 326a and 326b and the catalyst sections 315a and 315b. The shock absorbers contact the sensors on one side and the main housing in flange 389a, which comprise two flanges or section with threads to match the threads on the catalyst section 388a. The main housing may optionally contain the RH control system 333 as described in U.S. Pat. No. 6,251,344 herein incorporated by reference. The double-ended reservoir is further described in FIG. 6. The reservoir consists of chemicals encapsulated behind a grid that is covered with a membrane. The air with CO enters both sides through holes 310a and 310b (not shown). The dummy catalyst in section 315a does not change the CO concentration and the LED and photodiode can monitor optical changes as a result of CO and RH. The section 315b consumes the CO and thus the corresponding LED and photodiode measures the change in RH only. Thus by comparing the two different signals an accurate CO measurement can be determined.

Figure 4:
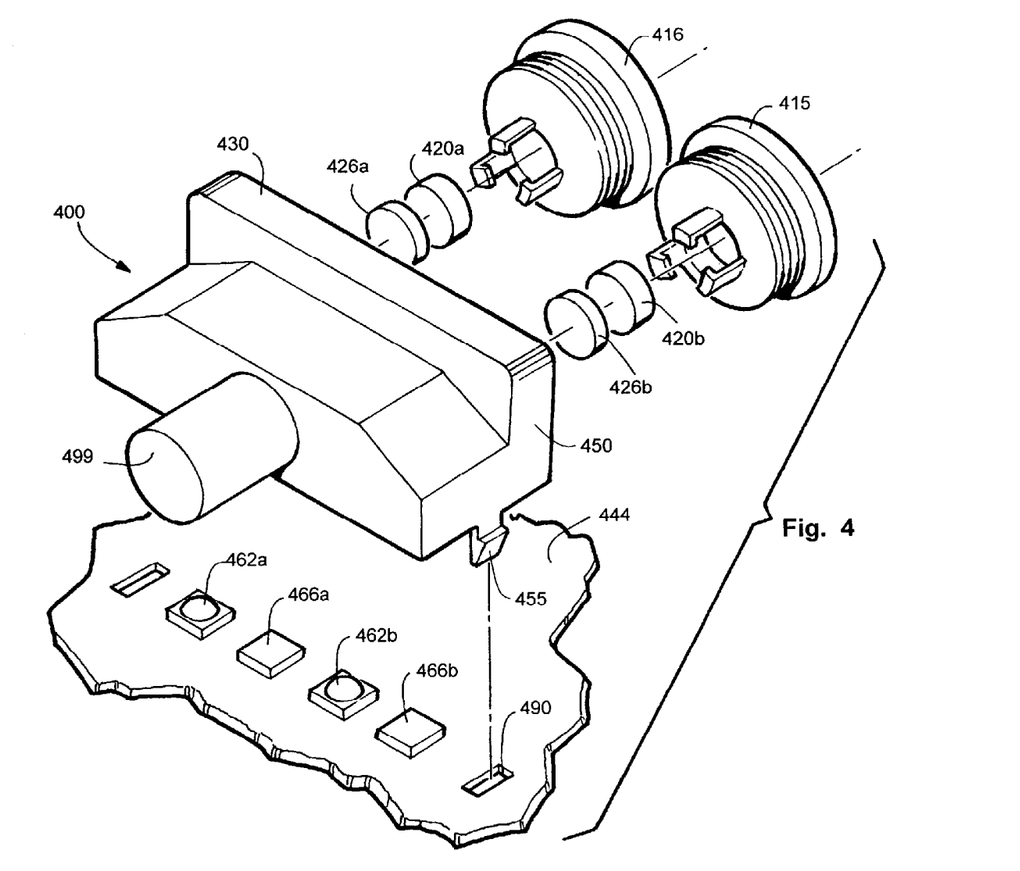
FIG. 4 illustrates a dual K sensor system with a common reservoir and a dummy catalyst and a catalyst.

FIG. 4 shows a sensor system 40 with 2 catalyst sections 416 and 415, respectively. These chambers 415 and 416 are connected by a common humidity chamber 499, which controls the change in RH and prevents very high RH. The RH chamber 499 may comprise chemicals that control the RH of both sensors 420a and 420b. The sensors may be held in place by some means such as fingers 424a and 424b on one side and a means such as a shock absorber, which is pressed against the inside flange 430 by a system of threads or other fasteners (not shown). There is a dummy catalyst in the in catalyst sections 415 and a real CO selective oxidation catalyst in the catalyst section 416 between the atmosphere and the sensors. The control sensor 420b is the control sensor that does not see CO because it is catalyzed to CO2. The dummy catalyst is in 416 and therefore that sensor 420a responds to CO. The advantage of this arrangement is that the RH modification due to the reservoir is the same for both sensors. There is a circuit board 444 that supports the sensing system 400 by holding the clips 455 on the main housing body 450. The LEDs 462a and 462b and mounted on the circuit board along with corresponding photodiodes 466a and 466b. The signal from the photodiodes can be processed to give accurate CO levels by removing the effect from the control sensor, which should be at the same rate as the CO sensor 420*a* because the diffusion rates are designed to be equal for both dummy and real catalyst.

Figure 5:
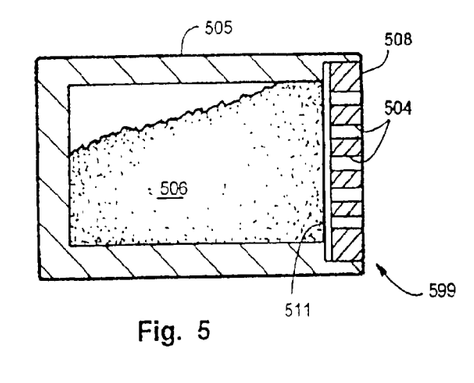
FIG. 5 illustrates a single end reservoir for controlling RH in a system such as that described in FIG. 4 above.

FIG. 5 depicts the cutaway view of a single-end reservoir system 599 comprising a case 505 that contains the chemical mixture 506; and further controls the RH in the sensor micro-environment (not shown) by means of the membrane 511 and the grid 508, which provides holes 504 by which water vapor may enter and leave after passing through the membrane on the way out of the reservoir.

Figure 6:
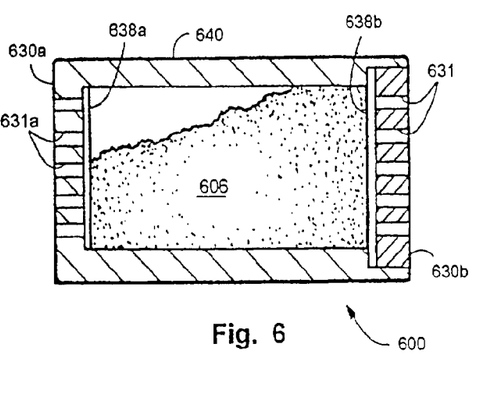
FIG. 6 illustrates a double end reservoir for controlling RH in a system such as that described in FIG. 3 above.

FIG. 6 depicts a two-ended reservoir 600 designed to control the RH in a two sensor micro-environment such as the system described in FIG. 3 above; and the system 600 further comprises two grids 630*a* and 630*b* both have a membrane welded to their frame as illustrated in the figure, which shows membrane 638*a* welded to grid 630*a* and membrane 638*b* welded to grid 630*b*, which in turn is welded to the main body 640 by photon welding or another joining method. The grids are joined to the ends of the main body 640 as shown. This may be by photon welding or any other suitable joining method; and further comprising a mixture of chemicals 606. The holes in the grid are label 631*a* and 631*b*. These holes are small so that the grid 630*a* and 630*b* will support the membrane 638*a* and 638*b*.

Figure 7:
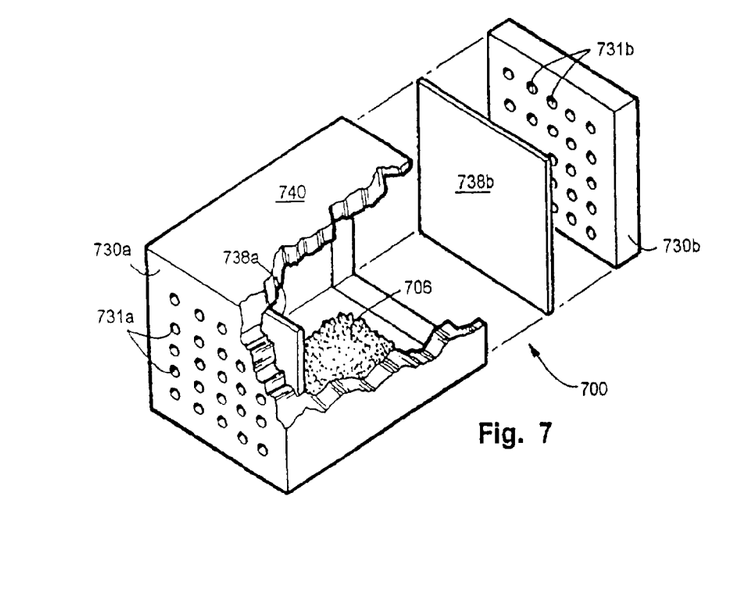
FIG. 7 is a three dimension view of reservoir in FIG. 6.

FIG. 7 is a three dimension view of reservoir in FIG. 6, which shows that the box like structure of the reservoir 700 is open to gas flow at each end but the membranes 738*a* and 738*b* prevent any liquid flow. The holes in the grid 731*a* and 731*b* are also illustrated. The center of the reservoir is filled with a chemical system 706. The outer structure 740 is joined to the grids 730*a* and 730*b* by some joining means such as photon welding. The system 700 is designed to withstand over 35-psi pressure on the inside, which can occur under high temperature high humidity conditions.

The chemical composition of the K sensor, which responds to CO and RH, is a high copper version of the S34 sensor with certain changes so only one sensor is needed. Typically, the chemical make up includes 0.102611 mmole of molydosilicic acid hydrate, 1.035984 mmole of calcium chloride dehydrate, 0.036192 mmole of trichloroacetic acid, 0.00208 mmole of copper trifluoroacetyl-acetonate, 0.244106 mmol of copper chloride dehydrate, 0.1144 mmol of calcium bromide dehydrate, 0.025151 mmole of sodium palladium chloride, 0.318475 mmole of palladium chloride, 0.015011 mmole of gamma cyclodextrin, 0.012928 mmole of hydroxypropyl-beta-cyclodextrin, and 0.007309 mmole of beta cyclodextrin. The pH of the solution may range from 0.1 to 1.5.

The main differences between the catalyst and the sensors are the concentration of copper in the formulation and in the types of substrate. The sensors utilize the SPS substrate, which is manufactured by Quantum Group. SPS are circular in shape. They are monolithic with the diameter about 0.230" in diameters and about 0.100" in thickness. Average pore diameter ranges from 23 nm to 28 nm. They are easily mounted for optical monitoring. The catalyst system used is similar chemistry with higher copper and may use a silica gel bead or granule substrate. However, the substrates may be SPS or crushed up SPS as well as the lower cost porous silica gel with very high surface area. The catalytic material is packed inside a column.

The K series sensor system described above may be used in a combined CO and smoke detector. The use of the fast responding K sensor, which enhances early fire detection by cross fertilization from one sensor system such as smoke to increase the sensitivity of the other. These types of fire detection may also incorporate other sensors such as heat, CO2, and hydrogen. An advantage to a multiple-sensing fire detector is to increase reliability and reduce false alarms. In one version of the fire detection system the photoelectric smoke sensor is combined with the smoke detector in a way that if photons are deflected or scattered by smoke particles, less photons are striking the photo-detector behind the K sensor. The scattered photons strike the dark photodetector sensor in the smoke circuit. The photons that are emitted from the photon source, in the absence of any particles go directly though the K sensor and the strike the light photo-detector such as a photodiode. If the CO sensor starts to get dark, then the smoke circuit is made more sensitive and vice versa.

A temperature sensor maybe placed outside the detection chamber, but attached to the alarm enclosure. The algorithm of the system is embedded in the micro-controller. The micro-controller receives, from the detection elements, signals of smoke. CO LED response though the K sensor and temperature. The embedded software does the calculations between these signals and makes the decision on the status of the environment regarding the temperature, the CO level, the relative humidity and smoke. A rapid raise in temperature and RH is an early indication of fire. The algorithm embedded in the micro-controller will decide when and if to trigger an alarm. The algorithm must contain the correlation between the four parameters in various fire situations, making this alarm respond in the fastest way, yet reduce any possible false alarm.

This CO/smoke has a light trapping fins that are curved so that smoke has access from all directions. This is an improvement over the CO/Smoke alarm described in U.S. Pat. No. 5,793,295 in which a dropping resistor is used to enhance the air flow through the smoke chamber with a heating chimney effect. Therefore the new device is useful for battery power; AC power; 12-volt low power system as well as AC with battery back up. Another major advantage of the K sensor system in fire detection is the ability to see that rapid rise in relative humidity. The K sensor system is capable of measuring both CO and relative humidity as described above. And combo- type detector is defined as one that also monitors temperature and humidity. Rapid rise in both RH and temperature indicates a serious combustion problem such as blocked flue or fire. When the combo-type detector features comprise temperature and smoke (ions and/or smoke particles) a more reliable early warning system is obtained for fire.

Those skilled in the art would readily appreciate that the scope of the invention is not limited to the presently preferred embodiment. For example, any number of properties of the sensor may be measured such as, for example, reflection of light from the sensor.

Also, one of ordinary skill in the art would recognize that any one of a variety of microprocessors and other circuit elements could be used to implement the invention, including those with built in analog to digital converters, or built in liquid crystal display drivers.

One skilled in the art would appreciate an apparatus and method for digitally tracking the response of optically responding sensors for a variety of target gases. Such an apparatus and method would increase the desirability of a wide variety of products from home-detectors to RV monitors to industrial controls.

Many other modifications and variations will be apparent to those skilled in the art, and it is therefore, to be understood that within the scope of the appended claims the invention may be practiced otherwise than as specifically described. The current products on the market that are battery operated use electrochemical cells for sensors. They are expensive, require frequent calibration, respond to interference gases and need frequent replacement. They will not operate in cold weather and therefore are not suited to cold climates. Metal Oxide Semiconductor sensors take very large amounts of power and therefore cannot be operated practically for most portable applications. Therefore, there is a need for a low cost, reliable, accurate, and easy to use battery-powered unit to detect CO and perform reliable fire detection.

What is claimed is:

1. A device for measuring the concentration of CO comprising a control sensor in an enclosure whose opening to the atmosphere is direct through a CO oxidation catalyst; and further comprising a CO responding sensor in an enclosure whose opening to the atmosphere is direct though a dummy catalyst that does not effect the CO concentration but has the same diffusion path as the catalyst, and further comprising optical responding sensors that can be monitored by a low-powered electronic circuit using light emitting diodes and photodiodes and further comprises sensors made of a supramolecular complex that is self assembled on to a porous substrate; and further comprising a sensing layer on the porous transparent substrate comprising palladium, copper, metals ions and cyclodextrins and their derivatives and an acid, the apparatus comprising means to detect CO and means for removing CO from the enclosed environment comprising a sensor, photon monitor, photon emitter, circuit, microprocessor, air circulation means catalyst to convert the CO to carbon dioxide is made immersing a porous silica gel material into a chemical reagent comprising at least one of the following groups: Group 1: Palladium salts selected from the group consisting of palladium salts of palladium chloride, palladium bromide, $CaPdCl_4$, $CaPdBr_4$, $Na_2PdCl_4$, $Na_2PdBr_4$, $K_2PdCl_4$, $K_2PdBr_4$, $Na_2PdBr_4$, $CaPdCl_xBr_y$, $K_2PdBr_xCl_y$, $Na_2PdBr_xCl_y$ (where x can be 1 to 3 if y is 4 or visa versa), and mixtures of any portion of all of the above: Group 2: Molybdenum salts selected from the group consisting of silicomolybdic acid, phosphomolybdic acids, and their soluble salts, alkaline earth metal salts of the molybdate anions, mixed heteropolymolybdates, or mixtures of any portion or all of the above: Group 3: Soluble salts of copper halides, nitrates, perchlorate, and mixtures thereof, copper organometallic compounds that regenerate the palladium including copper tetrafluoroacetic acid, copper triflouroacetylacetonate, and other similar copper compound, and any portion or all of the above; Group 4: Supramolecular complexing molecules selected from the cyclodextrin family including beta and gamma as well as their soluble derivatives including hydroymethyl, hydroxyethyl, and hydroxypropyl beta cyclodextrin, and their derivative, and mixtures of any portion or all of the above; Group 5: Soluble salts of alkaline and alkali halides, and certain transitional metal halides including manganese, cadmium, cobalt, chormimum, nickel, zinc, and other soluble halide including aluminum; and cerium oxide; and any mixture thereof: Group 6: Organic solvent and/or co-solvent and trifluorinated organic anion selected from the group including trichloroacetic acid, trifluoroacetate, a soluble metal trifluoroacetylacetonate selected from cation consisting of copper, calcium, magnesium, sodium, potassium, lithium, or mixture thereof; Group 7: Soluble inorganic acids including hydrochloric acid, nitric acid, and strong oxidizers including peroxide, or mixture thereof; and wherein the copper concentration is from 0.25 to 15,000 times the palladium concentration; and further processing the substrate by immersion into the solution containing the above substances; and removing from are slowly dried to allow a supramolecular complex to self assemble on the substrates surfaces to form the surpramolecular catalyst.

2. An apparatus as claimed in claim 1 for determining the carbon monoxide gas concentration comprising a means to incorporate the device into a new vehicle's manufacturing process; and further comprising a display to warn of a hazard, a means to indicate need for service; and further comprising an alarm that notifies the user visually or audibly of a hazard; and further comprising a chemical sensor comprising at least one of the following chemical groups; Group 1: Palladium salts selected from the group consisting of palladium chloride, palladium bromide, $CaPdCl_4$, $CaPdBr_4$, $Na_2PdCl_4$, $Na_2PdBr_4$, $K_2PdCl_4$, $K_2PdBr_4$, $Na_2PdBr_4$, $CaPdCl_xBr_y$, $K_3PdBr_xCl_y$, $Na_2PdBr_xCl_y$ and mixtures of any portion or all of the above; Group 2: Molybdenum acid salts selected from the group consisting of silicomolybdic acid, phosphomolybdic acids, and their soluble alkali metal and/or alkaline earth metal salts of the molybdate anions, mixed heteropolymolybdates and mixtures of any portion or all of the above; Group 3: Soluble salts of copper halides, nitrates, perchlorate, and mixtures thereof, copper organometallic compounds that regenerate the palladium including copper tetrafluoroacetic acid, copper triflouroacetylacetonate, and mixtures of any portion or all of the above; Group 4: Supramolecular complexing molecules selected from the cyclodextrin family including beta, and gamma as well as their soluble derivatives including hydroymethyl, hydroxyethyl, and hydroxypropyl beta cyclodextrin, and their derivative, and mixtures of any portion or all of the above; Group 5: Soluble salts of alkaline and alakli haldies, and certain transitional metal halides including cerium, manganese, cadmium, cobalt, chromium, nickel, zinc, and other soluble halide including aluminum; and any mixture thereof; Group 6: Organic solvent and/or co-solvent and trihalogenated organic acid, trichloroacetic acid, trifluoroacetate, a soluble metal trifluoracetylacetonate selected from cation consisting of copper, calcium and magnesium or mixture thereof; Group 7: Soluble inorganic acids including hydrochloric acid, nitric acid, and strong oxidizers including peroxide, or mixture thereof; and wherein the copper concentration is from 0.25 to 15 times the palladium concentration; and further processing the substrate by immersion into the solution containing the above substances and removing from are slowly dried to allow a supra-molecular complex to self assemble on the substrates surfaces to form the supramolecular catalyst.

3. An apparatus as claimed in claim 2 comprising a device, which sends a signal to other mechanisms, which could trigger an event such as opening or closing windows, turning on exhaust fans and/or opening and closing vents.

4. A device for measuring the concentration of CO comprising a control sensor in an enclosure whose opening to the atmosphere is direct through a CO oxidation catalyst; and further comprising a CO responding sensor in an enclosure whose opening to the atmosphere is direct though a dummy catalyst that does not effect the CO concentration but has the same diffusion path as the catalyst, and further comprising optical responding sensors that can be monitored by a low-powered electronic circuit using light emitting diodes and photodiodes and further comprises sensors made of a supramolecular complex that is self assembled on to a porous substrate; and further comprising a sensing layer on the porous transparent substrate comprising palladium, copper, metals ions and cyclodextrins and their derivatives and an acid, the apparatus measuring at least two target-gas concentrations where one is CO and the other is relative humidity; and further comprising a means to examine the changes in optical transmission from two different photon sources and further comprising a means to increase the reliability and speed of the fire detector; and further comprising a smoke detection means monitored by a low-powered electronic circuit with a current draw of less than 25 microamps in stand-by operation; and further comprises a supramolecular complex that is self assembled onto a porous substrate; and further comprising a sensing layer on the porous transparent substrate comprising palladium, copper, calcium metals ions and cyclodextrins and there derivatives and an acid.

5. A device for measuring the concentration of CO comprising a control sensor in an enclosure whose opening to the atmosphere is direct through a CO oxidation catalyst; and further comprising a CO responding sensor in an enclosure whose opening to the atmosphere is direct though a dummy catalyst that does not effect the CO concentration but has the same diffusion path as the catalyst, and further comprising optical responding sensors that can be monitored by a low-powered electronic circuit using light emitting diodes and photodiodes and further comprises sensors made of a supramolecular complex that is self assembled on to a porous substrate; and further comprising a sensing layer on the porous transparent substrate comprising palladium, copper, metals ions and cyclodextrins and their derivatives and an acid, the device comprising a smoke detector with the K series sensors for early detection of fires and reduce false alarms and further comprises a means to measure humidity and compensate the response of the K sensor for changes in RH, the device comprising a fire detector apparatus comprising an alarm signal means, power inlet or battery, enclosure with holes to let the sound escape and the smoke and gases enter, two independently pulsed photon sources, which emit photons through the sensor in the same general direction in short pulses at different times; and further comprising a photodetector optically coupled to read the independently pulsed photon sources located on the oppose side of the smoke chamber from the photon source and the photodetector design to detect photon scattering from the smoke particles with the optical responding CO sensor placed adjacent to far side photon detect; and further comprising a CO sensor that responds to CO and relative humidity, which can be calculated from two simple equations as described below;

And the values of the CO concentration and relative humidity are corrected for temperature by a temperature compensation means; and can be monitored by a low-powered electronic circuit with a current draw of less than 25 microamps in stand-by operation; and further comprises a CO relative humidity sensor consisting of supramolecular complex that is self assembled on to a porous substrate; and further comprising a very thin sensing layer on the porous transparent substrate comprising palladium, copper, calcium metals ions and cyclodextrins and there derivatives and an acid; and further comprising a means for sounding an alarm, a means for giving a visual signal, a means to power the circuit contained in the housing and a means to attach the housing to a wall, vehicle visor or ceiling, or install in an automobile, a circuit for measuring the photodector for determining intensity of photons passing through the sensor and the rate of change of photon pulse between intervals of the periodic pulses.

6. A device for measuring the concentration of CO comprising a control sensor in an enclosure whose opening to the atmosphere is direct through a CO oxidation catalyst; and further comprising a CO responding sensor in an enclosure whose opening to the atmosphere is direct though a dummy catalyst that does not effect the CO concentration but has the same diffusion path as the catalyst, and further comprising optical responding sensors that can be monitored by a low-powered electronic circuit using light emitting diodes and photodiodes and further comprises sensors made of a supramolecular complex that is self assembled on to a porous substrate; and further comprising a sensing layer on the porous transparent substrate comprising palladium, copper, metals ions and cyclodextrins and their derivatives and an acid, the apparatus sensing the presence of fires by monitoring the environment for carbon monoxide, smoke particles, ions, heat, and rapid rise in humidity comprising a K sensor, at least one infrared and one visible photon sources, and at least two photosensitive means for sensing the photons scattered by smoke particles and for sensing the changes in photon transmitted through the K sensor; at least one means for conducting current in an electric current relative to the photon intensity, wherein the photo-sensitive means is adapted for changing the current conduction when smoke particles are present between the light source and the normally dark photodetector means; means for sensing CO from the change in photon transmission in the near infrared; means for sensing water vapor from the change in photon transmission in the visible; a means for indicating the changes in transmission of CO and water vapor separately; and further comprising an enclosure that prevents photons from entering the sensing chamber; at least some means to power the circuit and a means to signal information about the status of any type hazardous condition detected.

7. An apparatus as claimed in claim 6 wherein at least one photon source is a laser diode.

8. An apparatus as claimed in claim 7 wherein the photon sources are directed primarily in one direction.

* * * * *

UNITED STATES PATENT AND TRADEMARK OFFICE
CERTIFICATE OF CORRECTION

PATENT NO. : 6,998,991 B1
APPLICATION NO. : 10/262047
DATED : February 14, 2006
INVENTOR(S) : Goldstein et al.

It is certified that error appears in the above-identified patent and that said Letters Patent is hereby corrected as shown below:

On the Title Page

| | |
|---|---|
| (57) Abstract, line 8 | Delete "flu", Insert --flue-- |
| (57) Abstract, line 11 | After "the CO", Insert --is-- |
| (57) Abstract, line 13 | After "increase", Insert --in-- |
| (57) Abstract, line 14 | After "combination", Insert --of-- |

In the Claims

| | |
|---|---|
| Column 15, line 15, Claim 1 | Delete "effect", Insert --affect-- |
| Column 15, line 23, Claim 1 | Delete "metals", Insert --metal-- |
| Column 15, lines 37-38, Claim 1 | Delete "of all of the above:", Insert --or all of the above;-- |
| Column 15, line 43, Claim 1 | Delete "above:" Insert --above;-- |
| Column 15, lines 46-47, Claim 1 | Delete "triflouroacetylacetonate", Insert --trifluoroacetylacetonate-- |
| Column 15, line 56, Claim 1 | Delete "chormimum", Insert --chromium-- |
| Column 16, line 5, Claim 1 | Delete "substrates", Insert --substrate-- |
| Column 16, line 18, Claim 2 | Delete "$K_3PdBr_xCl_y$", Insert --$K_2PdBr_xCl_y$-- |

UNITED STATES PATENT AND TRADEMARK OFFICE
CERTIFICATE OF CORRECTION

PATENT NO. : 6,998,991 B1
APPLICATION NO. : 10/262047
DATED : February 14, 2006
INVENTOR(S) : Goldstein et al.

It is certified that error appears in the above-identified patent and that said Letters Patent is hereby corrected as shown below:

| | |
|---|---|
| Column 16, line 27, Claim 2 | Delete "triflouroacetylacetonate", Insert --trifluoroacetylacetonate-- |
| Column 16, line 34, Claim 2 | Delete "alakli haldies", Insert --alkali halides-- |
| Column 16, line 60, Claim 4 | Delete "effect", Insert --affect-- |
| Column 17, line 2, Claim 4 | Delete "metals", Insert --metal-- |
| Column 17, lines 16-17, Claim 4 | Delete "metals ions and cyclodextrins and there", Insert --metal ions and cyclodextrins and their-- |
| Column 17, line 24, Claim 5 | Delete "effect", Insert --affect-- |
| Column 17, line 32, Claim 5 | Delete "metals", Insert --metal-- |
| Column 17, line 47, Claim 5 | Delete "oppose side", Insert --opposite side-- |
| Column 17, line 55, Claim 5 | Delete "And", Insert --and-- |
| Column 18, line 7, Claim 5 | Delete "there", Insert --their-- |
| Column 18, line 13, Claim 5 | Delete "photodector", Insert --photodetector-- |
| Column 18, line 21, Claim 6 | Delete "effect", Insert --affect-- |
| Column 18, line 29, Claim 6 | Delete "metals", Insert --metal-- |

UNITED STATES PATENT AND TRADEMARK OFFICE
CERTIFICATE OF CORRECTION

PATENT NO. : 6,998,991 B1
APPLICATION NO. : 10/262047
DATED : February 14, 2006
INVENTOR(S) : Goldstein et al.

It is certified that error appears in the above-identified patent and that said Letters Patent is hereby corrected as shown below:

Column 18, line 39, Claim 6      Delete "current",
Insert --circuit--

Signed and Sealed this

Thirtieth Day of January, 2007

JON W. DUDAS
*Director of the United States Patent and Trademark Office*